(12) United States Patent
Hosoi et al.

(10) Patent No.: US 7,690,790 B2
(45) Date of Patent: Apr. 6, 2010

(54) VISION TEST PATTERN INDICATOR

(75) Inventors: Yoshinobu Hosoi, Gamagori (JP); Yuichiro Kanazawa, Okazaki (JP)

(73) Assignee: Nidek Co., Ltd., Gamagori (JP)

( * ) Notice: Subject to any disclaimer, the term of this patent is extended or adjusted under 35 U.S.C. 154(b) by 28 days.

(21) Appl. No.: 12/225,156

(22) PCT Filed: Apr. 23, 2007

(86) PCT No.: PCT/JP2007/058725

§ 371 (c)(1),
(2), (4) Date: Sep. 16, 2008

(87) PCT Pub. No.: WO2007/125858

PCT Pub. Date: Nov. 8, 2007

(65) Prior Publication Data

US 2009/0213327 A1    Aug. 27, 2009

(30) Foreign Application Priority Data

Apr. 28, 2006  (JP)  .............................. 2006-126528

(51) Int. Cl.
*A61B 3/02* (2006.01)
(52) U.S. Cl. ....................................... 351/242; 351/239
(58) Field of Classification Search ................. 351/242, 351/239, 241, 246, 200
See application file for complete search history.

(56) References Cited

U.S. PATENT DOCUMENTS

| 4,863,258 | A |   | 9/1989 | Greene |
|---|---|---|---|---|
| 5,331,358 | A |   | 7/1994 | Schurle et al. |
| 5,436,681 | A | * | 7/1995 | Michaels ..................... 351/240 |
| 6,454,412 | B1 |   | 9/2002 | Torrey |
| 7,537,343 | B2 | * | 5/2009 | Kanazawa et al. .......... 351/239 |
| 7,607,778 | B2 | * | 10/2009 | Oda ........................... 351/240 |

FOREIGN PATENT DOCUMENTS

| JP | A 62-281920 | 12/1987 |
|---|---|---|
| JP | A 5-130975 | 5/1993 |
| JP | U 5-88501 | 12/1993 |

* cited by examiner

*Primary Examiner*—Hung X Dang
(74) *Attorney, Agent, or Firm*—Oliff & Berridge PLC

(57) ABSTRACT

A vision test pattern indicator is provided with a color display for displaying optotypes used for binocular vision tests which are conducted with a red filter set in front of an eye of an examinee and a green filter set in front of the other eye, and an arithmetic control part which controls the color display as a first optotype figure is displayed in a green color, a second optotype figure is displayed in a red color, a third optotype figure for fusion stimulus is displayed in a color excluding red and green components and a background of the optotypes is displayed in a white color.

5 Claims, 6 Drawing Sheets

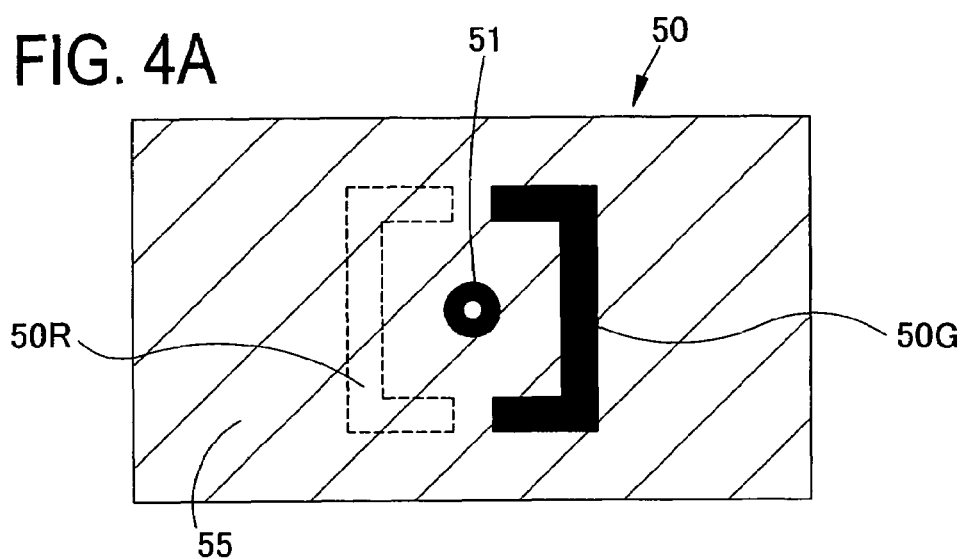
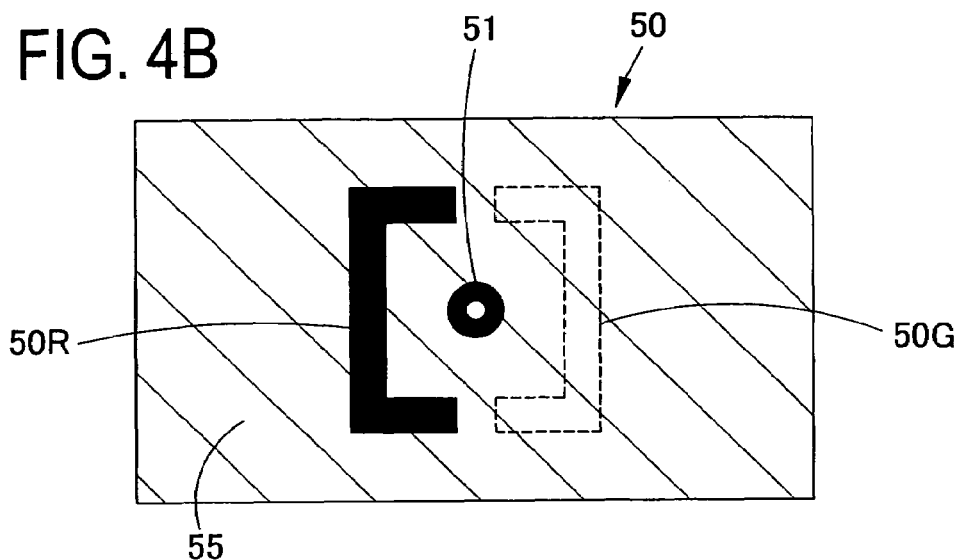
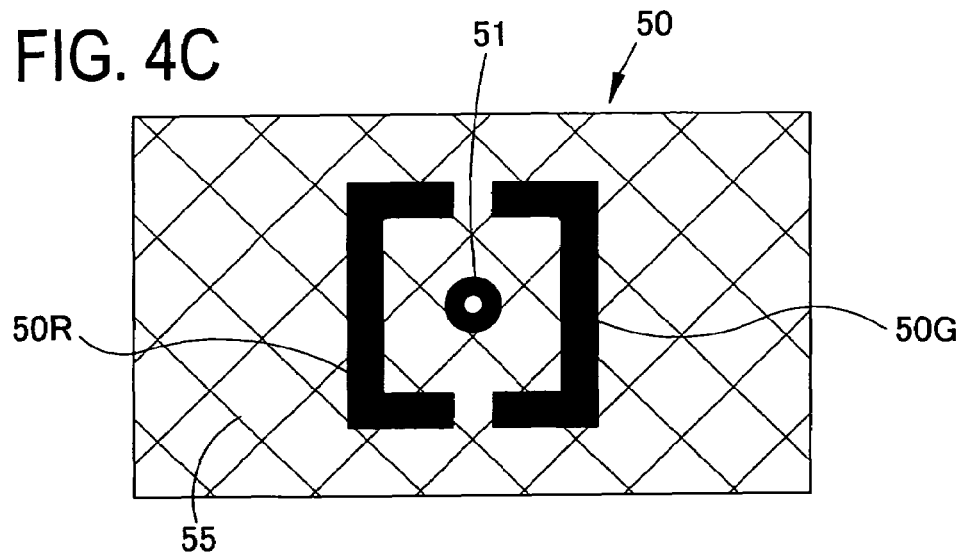

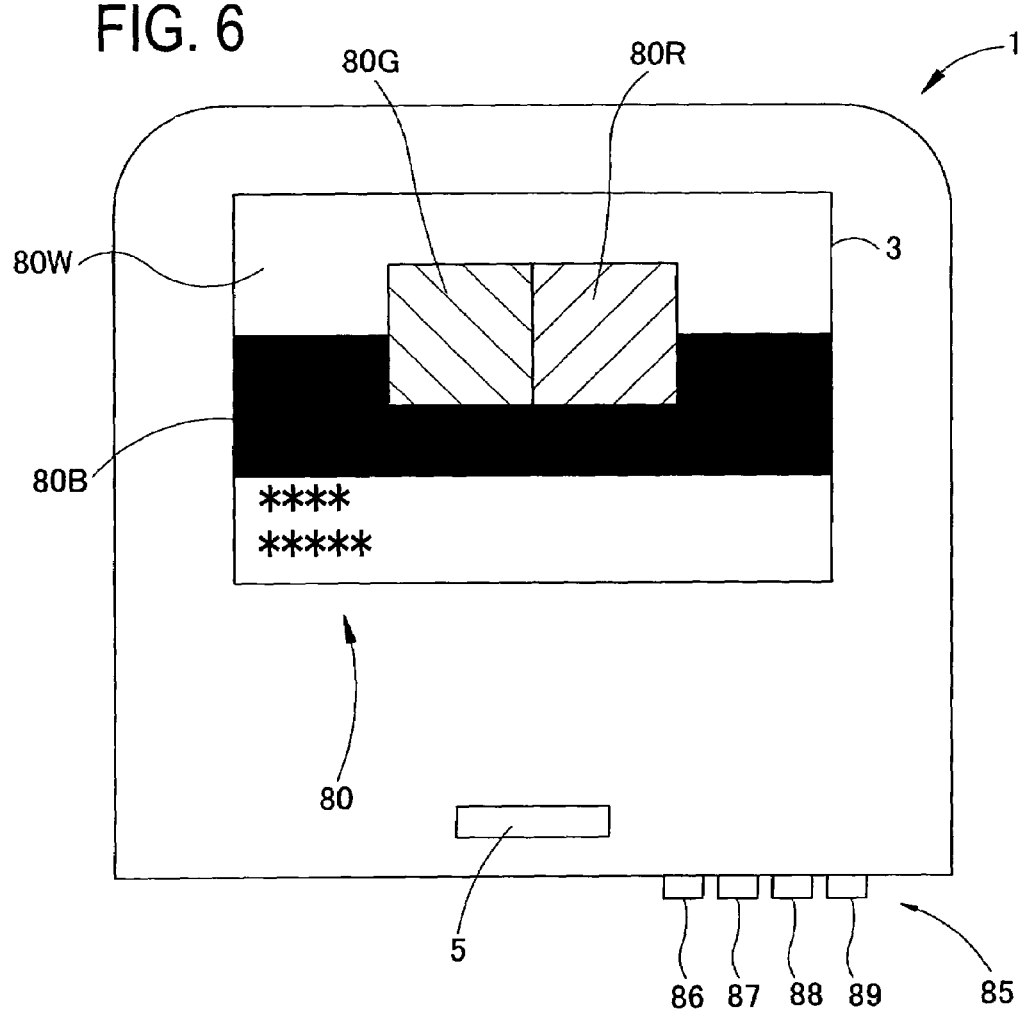

VISION TEST PATTERN INDICATOR

CROSS-REFERENCE TO RELATED APPLICATIONS

This is a national phase application based on the PCT International Patent Application No. PCT/JP2007/058725 filed on Apr. 23, 2007, the entire contents of which are incorporated herein by reference.

TECHNICAL FIELD

The present invention relates to a vision test pattern indicator (an optotype presenting apparatus) for presenting an optotype for testing visual functions of an examinee's eye.

BACKGROUND ART

As an optotype presenting apparatus, in addition to an apparatus of a conventional type arranged to project and present an optotype on a screen, an apparatus of another type arranged to present an optotype on a color liquid crystal display (LCD) has recently been proposed. One of apparatus using the LCD for binocular vision tests such as an aniseikonia test and a stereoscopic vision test has been proposed as an apparatus including two LCDs placed in tandem and two polarization filters having polarization axes perpendicular to each other. This apparatus is arranged, as with the conventional screen projection type apparatus, two polarization filters having polarization axes perpendicular to each other are set in front of both eyes of an examinee to present an optotype for right eye and an optotype for left eye to both eyes of the examinee (see U.S. Pat. No. 5,331,358 (JP5 (1993)-130975A)).

However, such configuration having two LCDs and two polarization filters is complicated and expensive and leads to a large-sized apparatus.

DISCLOSURE OF INVENTION

Problems to be Solved by the Invention

The present invention has a purpose to provide a vision test pattern indicator (an optotype presenting apparatus) simply configured capable of accurately performing a binocular vision test.

Means for Solving the Problems

To achieve the above purpose, the invention has the following characteristic configurations.

The vision test pattern indicator according to the invention comprises: a color display serving as a presenting part of an optotype for a binocular vision test to be performed with a red filter which is set in front of an eye of an examinee and a green filter which is set in front of the other eye; and an arithmetic control part adapted to control the color display to display a first figure of the optotype in green, a second figure of the optotype in red, a third figure for fusion stimulus of the optotype in a color excluding a red component and a green component, a background of the optotype in white.

In the vision test pattern indicator according to the invention, preferably, the optotype includes at least one of an optotype for an aniseikonia test and an optotype for a stereoscopic vision test.

In the vision test pattern indicator according to the invention, preferably, the third figure is displayed in black or blue.

Preferably, the vision test pattern indicator according to the invention further comprises adjusting means for adjusting a display color of the first figure and a display color of the second figure.

In the vision test pattern indicator according to the invention, preferably, the adjusting means comprises a color chart including a first sample showing the display color of the first figure, a second sample showing the display color of the second figure, a third sample showing a display color of the background, the color chart being to be displayed on the color display.

According to the vision test pattern indicator according to the invention, a binocular vision test can be accurately performed by a simple structure.

BRIEF DESCRIPTION OF DRAWINGS

FIG. 4A is a view showing how the optotype for an aniseikonia test appears;

FIG. 4B is another view showing how the optotype for an aniseikonia test appears;

FIG. 4C is another view showing how the optotype for an aniseikonia test appears;

FIG. 6 is a view showing a color balance control screen.

BEST MODE FOR CARRYING OUT THE INVENTION

Figure 1:
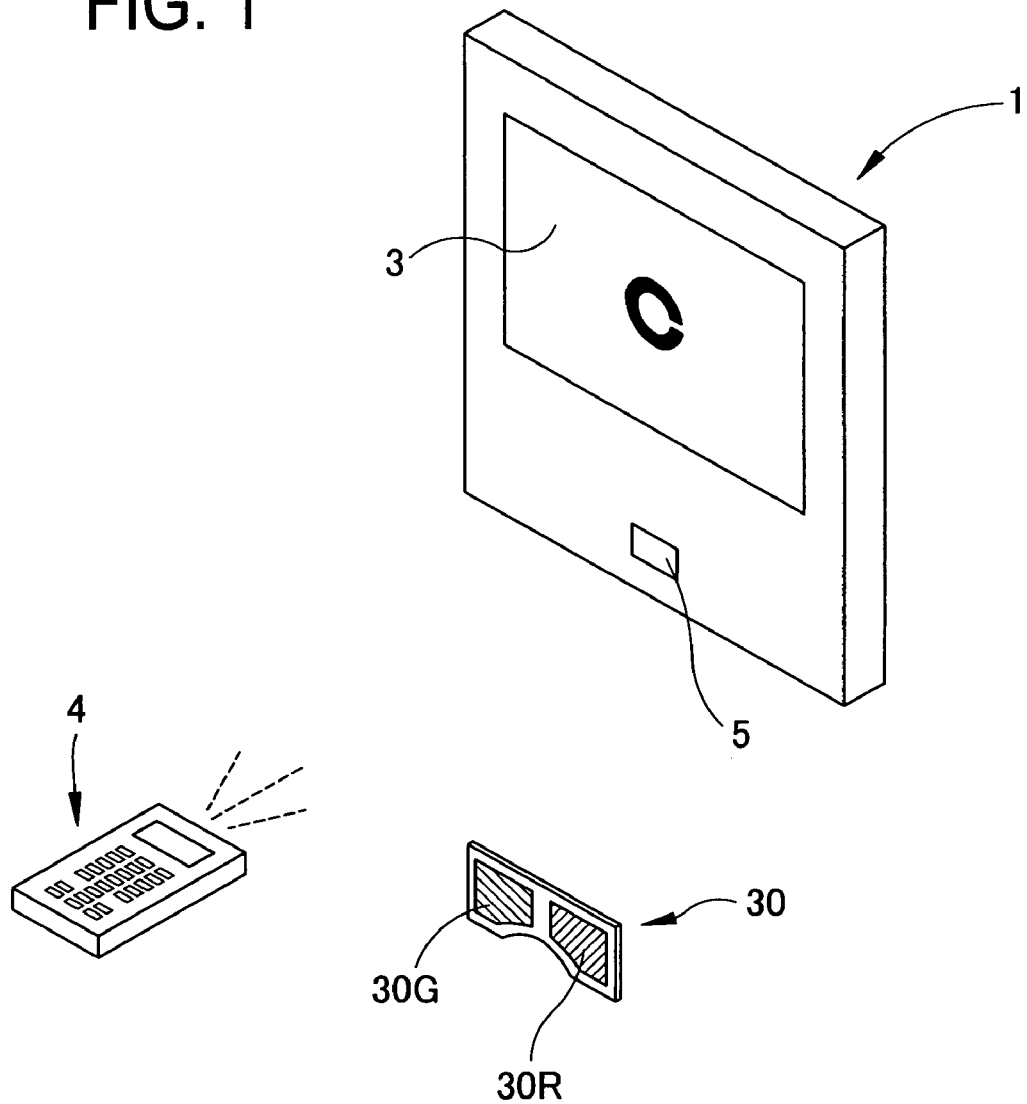
FIG. 1 is a schematic configuration view of an optotype presenting apparatus in a preferred embodiment of the invention.

A detailed description of a preferred embodiment of the present invention will now be given referring to the accompanying drawings. FIG. 1 is a schematic configuration view of an optotype presenting apparatus in the embodiment of the present invention.

A main unit 1 of the optotype presenting apparatus includes a presenting part 3 constituted of a color liquid display. The main unit 1 also includes a receiving part 5 which receives a signal from a remote controller 4. An optotype to be centrally displayed on the presenting part 3 is changed by operation of the controller 4.

A red/green spectacles 30 used for a binocular vision test has a red filter 30R for right eye and a green filter 30G for left eye.

Figure 2:
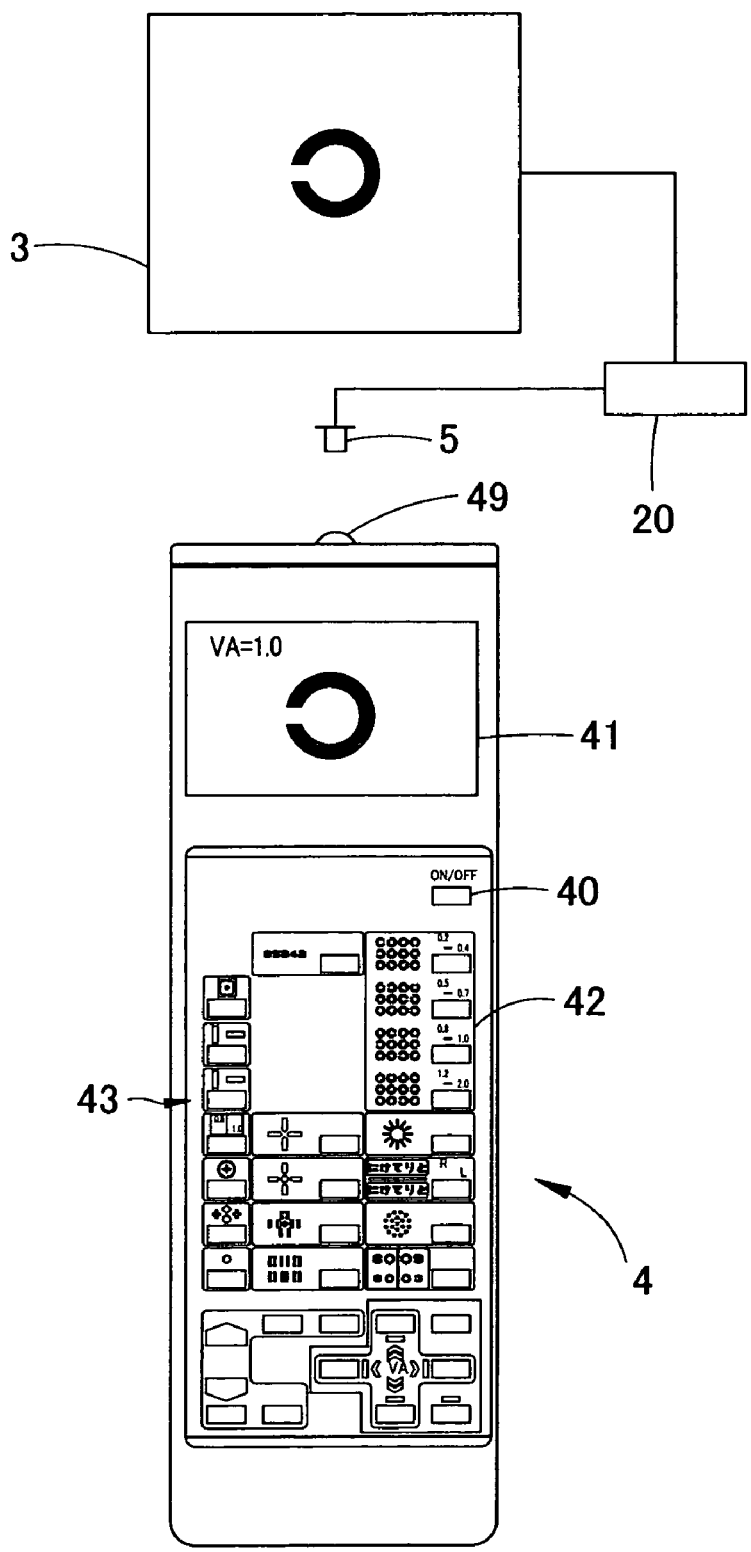
FIG. 2 is a schematic external view of a remote controller of the optotype presenting apparatus and a schematic block diagram of a control system of the optotype presenting apparatus.

FIG. 2 is a schematic external view of the controller 4 and a schematic block diagram of a control system of the optotype presenting apparatus. An arithmetic control part 20 of the optotype presenting apparatus (the main unit 1) is connected to the presenting part 3 and the receiving part 5. The arithmetic control part 20 includes a memory which stores various optotypes, a decoder circuit which decodes a signal from the controller 4, and others.

On the controller 4 there are arranged a plurality of operation buttons including a power button 40, optotype selector buttons 42 for a visual acuity test and optotype selector buttons 43 for a binocular vision test, and a display part 41 constituted of a color liquid display. By operation of the button 42, an optotype corresponding to a certain visual acuity is displayed on the presenting part 3 and the same optotype and its visual acuity are also displayed on the display part 41.

The binocular vision test using the above configured apparatus will be described. Firstly, an aniseikonia test is explained.

Figure 3A:
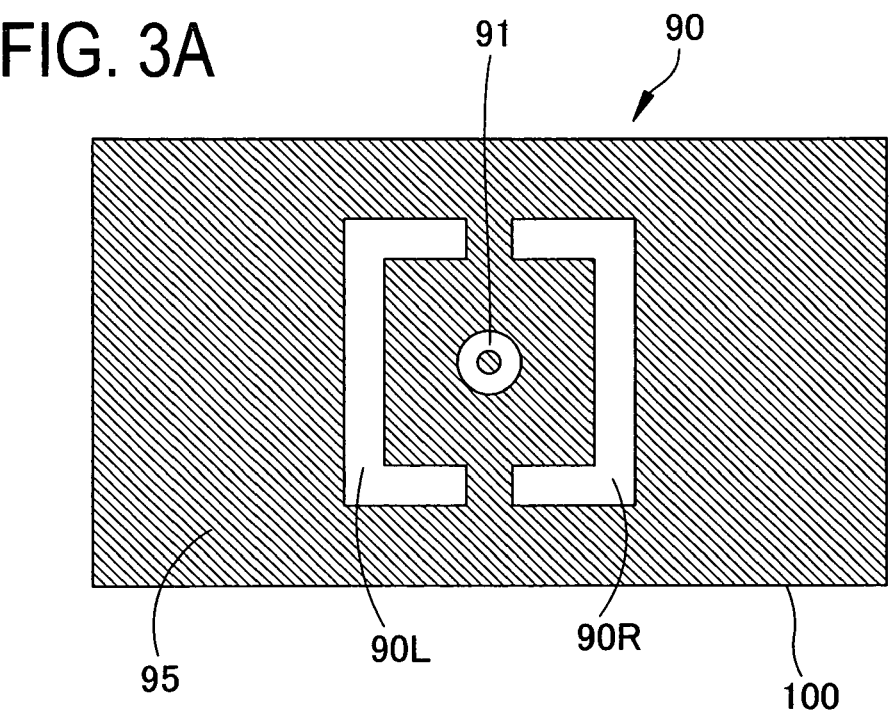
FIG. 3A is a view showing an optotype for an aniseikonia test.

An optotype 90 for an aniseikonia test projected and presented on a screen 100 by a conventional screen projection type apparatus has, as shown in FIG. 3A, a "]" shaped white FIG. 90R for right eye and having a 135° polarization direction, a "[" shaped white FIG. 90L for left eye, which is mirror-reversed from the FIG. 90R and has a 45° polarization direction, and a "○" shaped white FIG. 91 for both eyes, placed in the middle between the FIGS. 90R and 90L and having no polarization direction, those FIGS. 90R, 90L, and 91 being arranged on a black background 95 (the FIGS. 90R and 90L are symmetrical with respect to a vertical line passing the center of the FIG. 91). In the aniseikonia test, a polarization filter having a 135° polarization direction is placed in front of a right eye of the examinee and a polarization filter having a 45° polarization direction is placed in front of a left eye of the examinee.

Figure 3B:
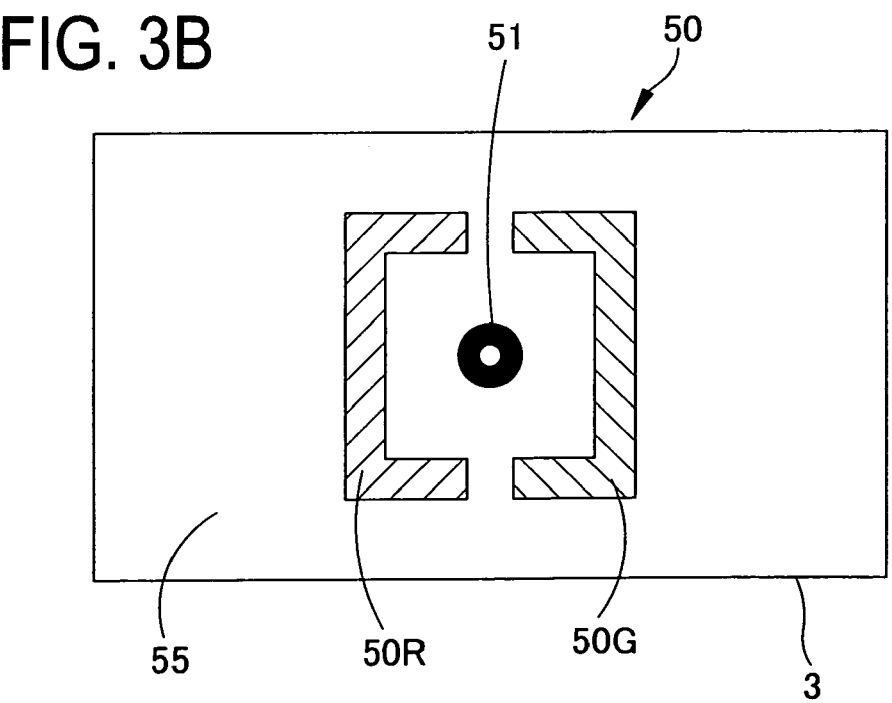
FIG. 3B is a view showing an optotype for an aniseikonia test.

On the other hand, an optotype 50 for an aniseikonia test displayed and presented on the presenting part 3 has, as shown in FIG. 3B, a "]" shaped green FIG. 50G for right eye and a "[" shaped red FIG. 50L for left eye, which is mirror-reversed from the FIG. 50G, and a "○" shaped black FIG. 51 for both eyes, placed in the middle between the FIGS. 50G and 50R, those FIGS. 50G, 50R, and 51 being arranged on a white background 55 (the FIGS. 50G and 50R are symmetrical with respect to a vertical line passing the center of the FIG. 51). The optotype 50 is displayed in such a way that the receiving part 5 receives a signal transmitted from a transmitting part 49 of the controller 4 by operation of a predetermined button of the buttons 43 and the arithmetic control part 20 controls the presenting part 3 based on the received signal.

When the examinee who wears the red/green spectacles 30 looks at the optotype 50, it appears like FIG. 4A to his/her right eye. Specifically, the right eye views the optotype 50 on the presenting part 3 through the red filter 30R and therefore the white background 55 appears red, the green FIG. 50G appears nearly black, the red FIG. 50R is blended into the background 55 and is almost invisible, and the black FIG. 51 appears black.

On the other hand, the optotype 50 appears like FIG. 4B to the left eye. Specifically, the left eye views the optotype 50 on the presenting part 3 through the green filter 30G and hence the white background 55 appears green, the green FIG. 50G is blended into the background 55 and is almost invisible, the red FIG. 50R appears nearly black, and the black FIG. 51 appears black.

Furthermore, the optotype 50 appears like FIG. 4C to both eyes. Specifically, the green FIG. 50G appears nearly black to the right eye, the red FIG. 50R appears nearly black to the left eye, and the black FIG. 51 appears black to both eyes.

In the case where the background 95 is black and the FIG. 91 for fusion stimulus is white, as in the conventional screen projection type apparatus, the FIG. 91 appears red to the right eye through the red filter 30R and the FIG. 91 appears green to the left eye through the green filter 30G. In other words, the "color" of fusion conditions "color, shape, size, and brightness" becomes different. Therefore, the FIG. 91 appearing in different colors may not be seen as a single figure by an examinee with weak fusion. This may affect a result of the aniseikonia test. On the other hand, when the background 55 is white and the fusion stimulus FIG. 51 is black as in the apparatus of the present embodiment, the FIG. 51 appears the same black to both the right eye and the left eye. Thus, the aniseikonia test can be performed accurately.

An explanation is given to a stereoscopic vision test as below.

Figure 5A:
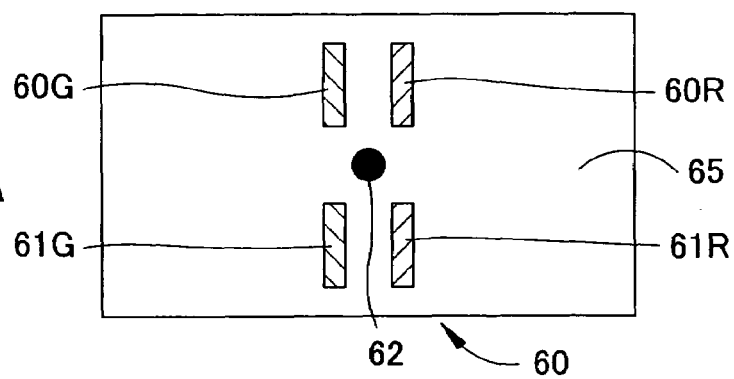
FIG. 5A is a view of an optotype for a stereoscopic vision test and how it appears.

An optotype 60 for a stereoscopic vision test displayed and presented on the presenting part 3 has, as shown in FIG. 5A, "|" shaped green FIGS. 60G and 61G for right eye, "|" shaped red FIGS. 60R and 61R for left eye, which are the same in shape as the FIGS. 60G and 61G, a "●" shaped black FIG. 62 for both eyes, placed in the center of the FIGS. 60G, 61G, 60R, and 61R, which are arranged on a white background 65 (the FIGS. 60G and 61G are symmetrical to the FIGS. 60R and 61R respectively with respect to a vertical line passing through the center of the FIG. 62, and the FIGS. 60G and 60R are symmetrical to the FIGS. 61G and 61R respectively with respect to a horizontal line passing through the center of the FIG. 62). The optotype 60 is displayed in such a way that the receiving part 5 receives a signal transmitted from the transmitting part 49 of the controller 4 by operation of a predetermined button of the buttons 43 and the arithmetic control part 20 controls the presenting part 3 based on the received signal.

Figure 5B:
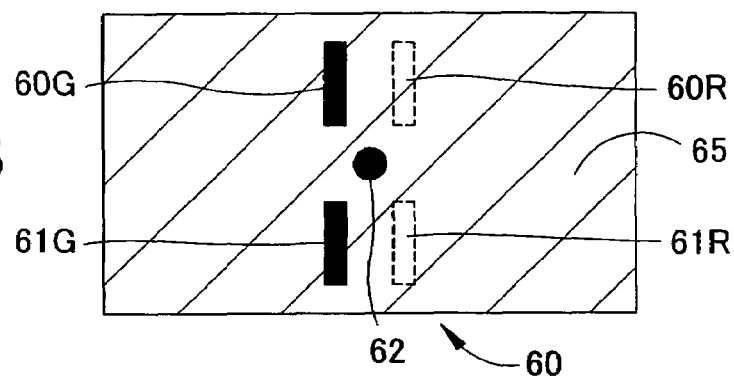
FIG. 5B is another view of the optotype for a stereoscopic vision test and how it appears.

When the examinee who wears the red/green spectacles 30 looks at the optotype 60, it appears like FIG. 5B to his/her right eye. Specifically, the right eye views the optotype 60 on the presenting part 3 through the red filter 30R and therefore the white background 65 appears red, the green FIGS. 60G and 61G appear nearly black, the red figures 60R and 61R are blended into the background 65 and are almost invisible, and the black FIG. 62 appears black.

Figure 5C:
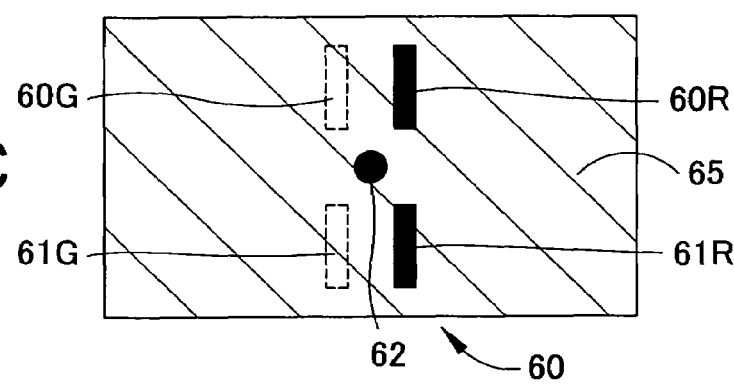
FIG. 5C is another view of the optotype for a stereoscopic vision test and how it appears.

On the other hand, the optotype 60 appears like FIG. 5C to the left eye. Specifically, the left eye views the optotype 60 on the presenting part 3 through the green filter 30G and hence the white background 65 appears green, the green FIGS. 60G and 61G are blended into the background 65 and are almost invisible, the red FIGS. 60R and 61R appear nearly black, and the black FIG. 62 appears black.

Figure 5D:
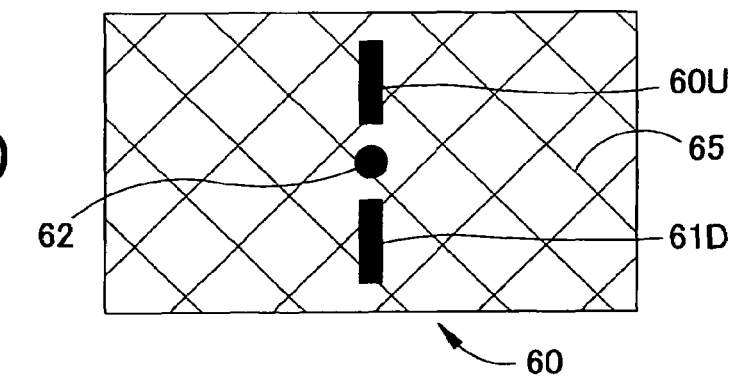
FIG. 5D is another view of the optotype for a stereoscopic vision test and how it appears.

Furthermore, the optotype 60 appears like FIG. 5D to both eyes. Specifically, the green FIGS. 60G and 61G appear nearly black to the right eye, the red FIGS. 60R and 61R appear nearly black to the left eye, and the black FIG. 62 appears black to both eyes. Furthermore, the FIGS. 60G and 60R appear to overlap each other as a nearly black FIG. 60U and the FIGS. 61G and 61R appear to overlap each other as a nearly black FIG. 60D.

In this case, as in the apparatus of the present embodiment, when the background 65 is white and the fusion stimulus FIG. 62 is black, the FIG. 62 appears the same black to both the right eye and the left eye. Thus, the stereoscopic vision test can be performed accurately.

The above description exemplifies the case where the red/green spectacles 30 having the red filter 30R and the green filter 30G is used, but not limited thereto. A phoroptor may also be used instead in which a red filter is set in a test window for right eye and a green filter is set in a test window for left eye.

Furthermore, the red filter 30R and the green filter 30G may be left-right reversely arranged. In this case, the green FIG. 50G (60G and 61G) and the red FIG. 50R (60R and 61R) are also arranged reversely.

The fusion stimulus FIGS. 51 and 62 are not limited to a black color and may be a blackish color when viewed through the red filter 30R and the green filter 30G, that is, a color excluding a red component and a green component, for example, blue or the like.

An explanation is given to a method for adjusting display luminance of the presenting part 3 (a color balance adjusting method) so that the red FIG. 50R (60R and 61R) is blended into the background 55 (65) appearing red when the optotype 50 (60) is viewed through the red filter 30R and the green FIG. 50G (60G and 61G) is blended into the background 55 (65) when the optotype 50 (60) is viewed through the green filter 30G.

FIG. 6 is a view showing a color chart 80 which is a screen for color balance adjustment displayed on the presenting part 3. Four function buttons 85 are arranged at the bottom of the main unit 1. The color chart 80 is displayed by operation of a menu button 86 of the buttons 85. In almost the center of the color chart 80, a red sample 80R and a green sample 80G are arranged and their lower portions are surrounded by a black sample 80B and their upper portions are surrounded by a white sample 80W. The red sample 80R shows a display color of the red FIG. 50R (60R and 61R), the green sample 80G shows a display color of the green FIG. 50G (60G and 61G), the black sample 80B shows a display color of the black FIG. 51 (62), and the white sample 80W shows a display color of the background 55 (65). Those samples 80R, 80G, 80W, and 80B are controlled in combination of a red component, a green component, and a blue component.

To blend the red FIG. 50R (60R and 61R) in the background 55 (65) appearing red when the optotype 50 (60) is viewed through the red filter 30R, the color chart 80 is displayed by operation of the button 86, the "red" is chosen by operation of a selection button 87 of the buttons 85, and luminance and others of the red component of the red sample 80R is changed (increased or decreased) by operating a plus button 88 and a minus button 89 of the buttons 85 while observing the color chart 80 through the red filter 30R so that the red sample 80R is blended into the white sample 80W.

To blend the green FIG. 50G (60G and 61G) into the background 55 (65) appearing green when the optotype 50 (60) is viewed through the green filter 30G, the color chart 80 is displayed, the "green" is chosen, and luminance and others of the green component of the green sample 80G is changed (increased or decreased) while observing the color chart 80 through the green filter 30G so that the green sample 80G is blended into the white sample 80W.

The invention claimed is:

1. A vision test pattern indicator, comprising:
   a color display serving as a presenting part of an optotype for a binocular vision test to be performed with a red filter which is set in front of an eye of an examinee and a green filter which is set in front of the other eye; and
   an arithmetic control part adapted to control the color display to display a first figure of the optotype in green, a second figure of the optotype in red, a third figure for fusion stimulus of the optotype in a color excluding a red component and a green component, a background of the optotype in white.

2. The vision test pattern indicator according to claim 1, wherein
   the optotype includes at least one of an optotype for an aniseikonia test and an optotype for a stereoscopic vision test.

3. The vision test pattern indicator according to claim 1, wherein
   the third figure is displayed in black or blue.

4. The vision test pattern indicator according to claim 1, further comprising adjusting means for adjusting a display color of the first figure and a display color of the second figure.

5. The vision test pattern indicator according to claim 4, wherein
   the adjusting means comprises a color chart including a first sample showing the display color of the first figure, a second sample showing the display color of the second figure, a third sample showing a display color of the background, the color chart being to be displayed on the color display.

* * * * *